United States Patent
Tong et al.

(10) Patent No.: US 10,660,527 B2
(45) Date of Patent: May 26, 2020

(54) BLOOD VESSEL IMAGING TEMPERATURE MEASUREMENT METHOD

(71) Applicant: Hetaida Technology Co., Ltd., Dongguan, Guangdong (CN)

(72) Inventors: Yaonan Tong, Yueyang (CN); Zhenguang Chen, Dongguan (CN); Song Chen, Yueyang (CN); Zhaoming Luo, Yueyang (CN); Feng Zhou, Yueyang (CN); Xuanbing Yang, Yueyang (CN)

(73) Assignees: HETAIDA TECHNOLOGY CO., LTD., Dongguan, Guangdong (CN); HUNAN INSTITUTE OF SCIENCE AND TECHNOLOGY, Yueyang, Hunan (CN)

( * ) Notice: Subject to any disclaimer, the term of this patent is extended or adjusted under 35 U.S.C. 154(b) by 226 days.

(21) Appl. No.: 15/813,159

(22) Filed: Nov. 15, 2017

(65) Prior Publication Data

US 2019/0046043 A1 Feb. 14, 2019

(30) Foreign Application Priority Data

Aug. 8, 2017 (CN) .......................... 2017 1 0672248

(51) Int. Cl.
| | |
|---|---|
| *A61B 5/01* | (2006.01) |
| *G01K 13/02* | (2006.01) |
| *G01K 1/14* | (2006.01) |
| *G01K 13/00* | (2006.01) |
| *G01J 5/00* | (2006.01) |
| *A61B 5/024* | (2006.01) |
| *A61B 5/00* | (2006.01) |
| *A61B 5/02* | (2006.01) |

(52) U.S. Cl.
CPC ............ *A61B 5/01* (2013.01); *A61B 5/02416* (2013.01); *A61B 5/489* (2013.01); *G01J 5/0025* (2013.01); *G01K 1/14* (2013.01); *G01K 13/002* (2013.01); *G01K 13/02* (2013.01); *A61B 5/0077* (2013.01); *A61B 5/02007* (2013.01); *A61B 5/742* (2013.01)

(58) Field of Classification Search
CPC ....... A61B 5/01; A61B 5/015; A61B 5/02416; A61B 5/489; A61B 5/0077; A61B 5/02007; A61B 5/742; A61B 8/085
See application file for complete search history.

(56) References Cited

U.S. PATENT DOCUMENTS 5,115,815 A * 5/1992 Hansen ..................... A61B 5/01 374/121
5,678,555 A * 10/1997 O'Connell ............... A61B 5/01 600/473

(Continued)

*Primary Examiner* — Lisa M Caputo
*Assistant Examiner* — Philip L Cotey
(74) *Attorney, Agent, or Firm* — Leong C. Lei

(57) ABSTRACT

A blood vessel imaging temperature measurement method is provided. The method comprises the steps of finding blood vessels, displaying a measurement position, and aligning for temperature measurement to achieve visual and precision temperature measurement. The temperature measurement is quite visual, instead of the traditional technology that uses a blind measurement method corresponding to a position to be measured, thereby solving the problem that the temperature measurement is not accurate enough in the traditional technology.

10 Claims, 3 Drawing Sheets

(56) References Cited

U.S. PATENT DOCUMENTS

| | | | | |
|---|---|---|---|---|
| 8,489,178 B2* | 7/2013 | Wood | ............... | A61B 5/0059 600/473 |
| 8,811,692 B2* | 8/2014 | Prokoski | ............... | A61B 5/0064 382/128 |
| 9,199,082 B1* | 12/2015 | Yared | ............... | A61N 1/05 |
| 2003/0047683 A1* | 3/2003 | Kaushal | ............... | G02B 23/12 250/330 |
| 2004/0006277 A1* | 1/2004 | Langenhove | ............... | A61B 5/01 600/481 |
| 2008/0045818 A1* | 2/2008 | Wood | ............... | A61B 5/0059 600/310 |
| 2010/0191124 A1* | 7/2010 | Prokoski | ............... | A61B 5/0064 600/473 |
| 2011/0066035 A1* | 3/2011 | Norris | ............... | A61B 1/00096 600/478 |
| 2014/0236019 A1* | 8/2014 | Rahum | ............... | A61B 5/0075 600/473 |
| 2015/0112260 A1* | 4/2015 | David | ............... | A61B 5/015 604/116 |
| 2016/0113517 A1* | 4/2016 | Lee | ............... | G01J 5/0859 600/474 |
| 2018/0005085 A1* | 1/2018 | Kakileti | ............... | A61B 5/0075 |

* cited by examiner

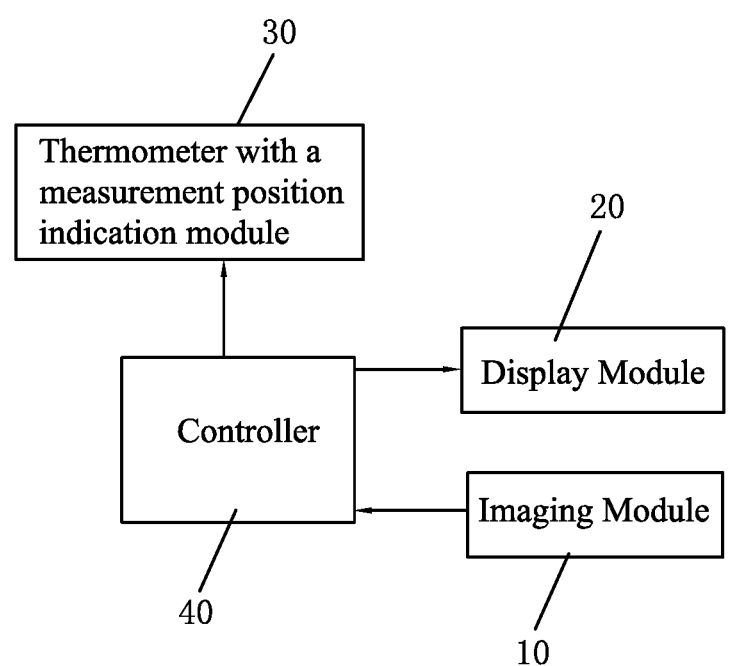
F I G. 1

BLOOD VESSEL IMAGING TEMPERATURE MEASUREMENT METHOD

BACKGROUND OF THE INVENTION

1. Field of the Invention

The present invention relates to body temperature measurement, and more particularly to a blood vessel imaging temperature measurement method.

2. Description of the Prior Art

The measurement of the human body temperature is taken by blind measurement, that is, the measurement position is only an approximate area. For example, infrared measurement is used to measure the temperature of the forehead. In fact, the temperature of the arteries can best reflect the body temperature. However, people do not know the vascular accurate position when measuring the human body temperature. The measurement is performed corresponding to an approximate position, that is, the aforementioned "blind measurement". As a result, the accuracy of the human body temperature measurement is limited.

The applicant of this application has carefully studied a new technical scheme. By visualizing the blood vessels of the human body in the form of an image on the surface of the skin, visual set-point temperature measurement is performed to align with the blood vessels of the required measurement, improving the measurement accuracy and measurement reliability of the human body temperature.

SUMMARY OF THE INVENTION

In view of the shortcomings of the prior art, the primary object of the present invention is to provide a blood vessel imaging temperature measurement method to achieve visual and precision temperature measurement. The measurement is quite visual, instead of the traditional technology that uses a blind measurement method corresponding to a position to be measured. The present invention solves the problem that the temperature measurement is not accurate enough in the traditional technology.

According to one aspect of the present invention, a blood vessel imaging temperature measurement method is provided. The method comprises the steps of:

(1) finding blood vessels: using an imaging module to image a true arrangement of blood vessels of a required temperature measurement area;

(2) displaying a measurement position: using a display module to project the blood vessels of the required temperature measurement area onto the required temperature measurement area, the blood vessels of the required temperature measurement area being marked in the form of an image on a skin outer surface;

(3) aligning for temperature measurement: using a thermometer with a measurement position indication module to perform visual set-point temperature measurement; wherein, the measurement position indication module indicates a specific blood vessel position required for measurement in alignment with the image of the blood vessels;

using a controller to obtain an image signal according to the imaging module and projecting it on the display module, the thermometer with the measurement position indication module performing visual set-point temperature measurement based on a displayed blood vessel image.

According to another aspect of the present invention, a blood vessel imaging temperature measurement method is provided. The method comprises the steps of:

(1) finding blood vessels: using an imaging module to image a true arrangement of blood vessels of a required temperature measurement area;

(2) displaying a measurement position: analyzing and obtaining a required measurement target area according to the true arrangement of the blood vessels obtained by the imaging module, using a display module to mark the required measurement target area on a skin outer surface;

(3) aligning for temperature measurement, using a thermometer with a measurement position indication module to perform visual set-point temperature measurement; wherein, the measurement position indication module indicates a marked position in alignment with the required measurement target area;

using a controller to obtain an image signal according to the imaging module and projecting it on the display module, the thermometer with the measurement position indication module performing visual set-point temperature measurement based on a measurement target area mark.

Preferably, the imaging module is one of an infrared thermal imaging module, a velocity vector imaging module, a CCD imaging module, and a COMS imaging module.

Preferably, the display module is a projection module.

Preferably, the measurement position indication module includes an indicator lamp for indicating a temperature measurement position.

Preferably, the indicator lamp is one of an LED lamp and a laser lamp.

The present invention has obvious advantages and beneficial effects compared with the prior art. In particular, the method comprises the steps of finding blood vessels, displaying a measurement position, and aligning for temperature measurement. The visual set-point temperature measurement is performed based on the displayed blood vessel image or the measurement target area mark. The measurement is quite visual, instead of the traditional technology that uses a blind measurement method corresponding to a position to be measured. The present invention solves the problem that the temperature measurement is not accurate enough in the traditional technology and improves the measurement accuracy and measurement reliability for the human body temperature.

BRIEF DESCRIPTION OF THE DRAWINGS

FIG. 1 is a block diagram showing the structural connection in accordance with an embodiment of the present invention;

DETAILED DESCRIPTION OF THE PREFERRED EMBODIMENTS

Embodiments of the present invention will now be described, by way of example only, with reference to the accompanying drawings.

Figure 2:
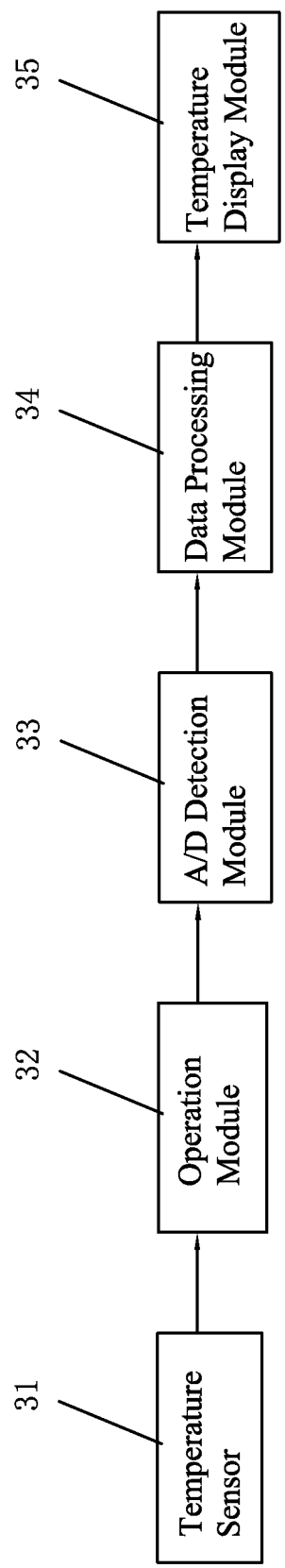
FIG. 2 is a block diagram showing the connection of the internal modules of the thermometer in accordance with an embodiment of the present invention.
Figure 3:
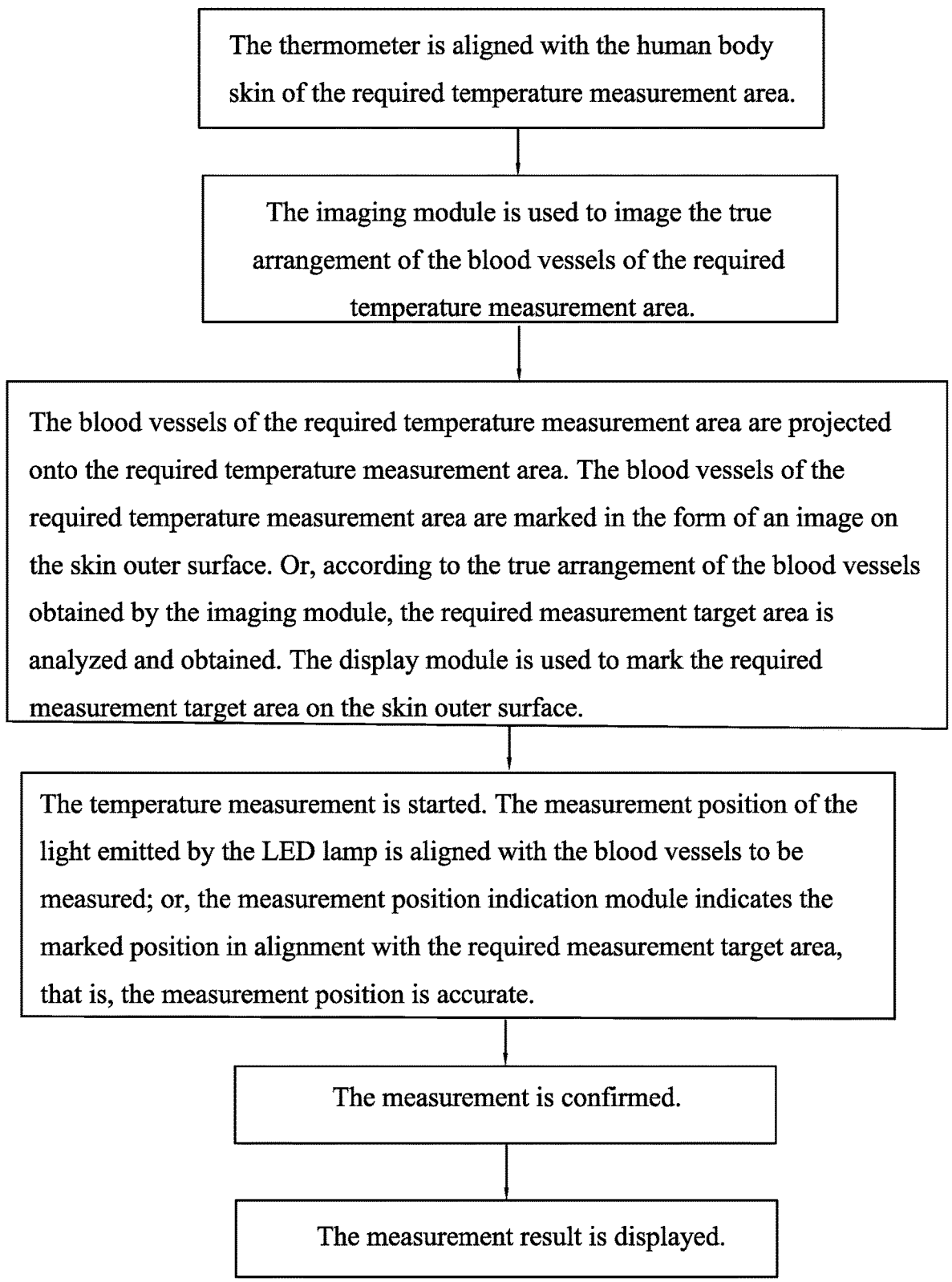
FIG. 3 is a block diagram showing the temperature measurement steps in accordance with an embodiment of the present invention.

Referring to FIG. 1 to FIG. 3, there is shown a specific structure of an embodiment of the present invention.

A blood vessel imaging temperature measurement system includes an imaging module 10, a display module 20, a thermometer 30 with a measurement position indication module, and a controller 40. The controller 40 is connected with the imaging module 10 and the display module 20. The controller 40 obtains an image signal according to the imaging module 10 and projects it on the display module 20. The thermometer 30 with the measurement position indication module performs visual set-point temperature measurement based on a displayed blood vessel image or a measurement target area mark.

In this embodiment, the imaging module 10 is an infrared thermal imaging module, a velocity vector imaging module, a CCD imaging module, or a COMS imaging module. The display module 20 is a projection module or the like. The measurement position indication module includes an indicator lamp for indicating a temperature measurement position. The indicator lamp is an LED lamp or a laser lamp. When the specific products are designed, the imaging module 10, the display module 20 and the measurement position indication module are not limited to the above-described designs. The present invention mainly includes these functional modules, the imaging module 10, the display module 20, and the thermometer 30 with the measurement position indication module. These functional modules are combined with the controller 40 to achieve visual precision temperature measurement. As for the specific designs of the functional modules, there may be a variety of different situations.

Next, a method for temperature measurement by using the aforesaid blood vessel imaging temperature measurement system will be described in detail. The human body temperature measurement is taken as an example in this description. The method comprises the following steps of:

(1) Finding blood vessels: The thermometer is aligned with the human body skin of the required temperature measurement area. The imaging module 10 is used to image the true arrangement of the blood vessels of the required temperature measurement area.

(2) Displaying a measurement position: The blood vessels of the required temperature measurement area are projected onto the required temperature measurement area by the display module 20. The blood vessels of the required temperature measurement area are marked in the form of an image on a skin outer surface. In this way, the arrangement of the real blood vessels of the human body is displayed in the form of an image on the skin surface of the human body. The image and the arrangement of the real blood vessels are exactly the same, which is quite visual.

(3) Aligning for temperature measurement: The thermometer 30 with the measurement position indication module is used to perform the visual set-point temperature measurement. Wherein, the measurement position indication module indicates a specific blood vessel position required for measurement in alignment with the image of the blood vessels. Based on the image formed in step (2), the user only needs to accurately measure the displayed blood vessels on the image corresponding to the skin surface of the human body. It usually uses the human eye to judge. The measurement position of the light emitted by the indicator lamp is well aligned with the blood vessels to be measured, that is, the measurement position is accurate and then measured.

In step (2) of displaying measurement position, it is also possible to analyze and obtain the required measurement target area according to the true arrangement of the blood vessels obtained by the imaging module. The required measurement target area is marked on the skin surface of the human body by using the display module. In this way, in step (3) of aligning for temperature measurement, the measurement position indication module indicates the marked portion in alignment with the required measurement target area to achieve the visual set-point temperature measurement. The manner to mark the measurement target area is simpler in comparison with the manner that the true arrangement of the blood vessels of the human body is displayed in the form of an image on the skin surface of the human body, and the user does not need to judge the position of the specific blood vessels to be measured. The requirement for the user is low. This manner is practical and better. The same product may be combined with the aforesaid two display measurement manners. The user can choose one of the two display measurement manners as desired. It can be combined with the two display measurement manners, that is, the target area is marked on the image of the blood vessels.

The thermometer 30 with the measurement position indication module has a temperature sensor 31, an operation module 32, an A/D detection module 33, a data processing module 34 and a temperature display module 35 which are connected in sequence. The temperature display structure can be displayed directly through the temperature display module 35 (such as a display) on the thermometer product for the user to read and review. Through Bluetooth, WiFi, RF or other wireless ways, the measured temperature results are sent to a smart mobile terminal, such as a mobile phone, so that the user can review and save the records through the APP of the smart mobile terminal.

In summary, the feature of the present invention is that the method comprises the steps of finding blood vessels, displaying a measurement position, and aligning for temperature measurement. The visual set-point temperature measurement is performed based on the displayed blood vessel image or the measurement target area mark. The measurement is quite visual, instead of the traditional technology that uses a blind measurement method corresponding to a position to be measured. The present invention solves the problem that the temperature measurement is not accurate enough in the traditional technology and improves the measurement accuracy and measurement reliability for the human body temperature.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A blood vessel imaging temperature measurement method, comprising the steps of:
   (1) finding blood vessels: using an imager to image a true arrangement of blood vessels of a required temperature measurement area;
   (2) displaying a measurement position: using an image display to display, through projection, an image of the blood vessels of the required temperature measurement area onto the required temperature measurement area, such that the image of the blood vessels of the required temperature measurement area is marked on a skin surface; and
   (3) aligning for temperature measurement: using a thermometer with a measurement position indicator to perform visual set-point temperature measurement, wherein the measurement position indicator indicates a specific blood vessel position required for measurement in alignment with the image of the blood vessels;

wherein a controller is operable to obtain an image signal according to the imager and displays the image signal, through projection, with the image display, and the thermometer with the measurement position indicator performs visual set-point temperature measurement based on a displayed blood vessel image.

2. The blood vessel imaging temperature measurement method as claimed in claim 1, wherein the imager is one of an infrared thermal imager, a velocity vector imager, a charge-coupled device (CCD) imager, and a continuous opacity monitoring system (CMOS) imager.

3. The blood vessel imaging temperature measurement method as claimed in claim 1, wherein the image display is a projector.

4. The blood vessel imaging temperature measurement method as claimed in claim 1, wherein the measurement position indicator includes an indicator lamp for indicating a temperature measurement position.

5. The blood vessel imaging temperature measurement method as claimed in claim 4, wherein the indicator lamp is one of a light-emitting diode (LED) lamp and a laser lamp.

6. A blood vessel imaging temperature measurement method, comprising the steps of:
  (1) finding blood vessels: using an imager to image a true arrangement of blood vessels of a required temperature measurement area;
  (2) displaying a measurement position: analyzing and obtaining a required measurement target area according to the true arrangement of the blood vessels obtained by the imager, using an image display to mark the required measurement target area on a skin surface;
  (3) aligning for temperature measurement, using a thermometer with a measurement position indicator to perform visual set-point temperature measurement, wherein the measurement position indicator indicates a marked position in alignment with the required measurement target area;
  wherein a controller is operable to obtain an image signal according to the imager and displays the image signal, through projection, with the image display, and the thermometer with the measurement position indicator performs visual set-point temperature measurement based on a measurement target area mark.

7. The blood vessel imaging temperature measurement method as claimed in claim 6, wherein the imager is one of an infrared thermal imager, a velocity vector imager, a charging coupled device (CCD) imager, and a continuous opacity monitoring system (CMOS) imager.

8. The blood vessel imaging temperature measurement method as claimed in claim 6, wherein the image display is a projector.

9. The blood vessel imaging temperature measurement method as claimed in claim 6, wherein the measurement position indicator includes an indicator lamp for indicating a temperature measurement position.

10. The blood vessel imaging temperature measurement method as claimed in claim 9, wherein the indicator lamp is one of a light-emitting diode (LED) lamp and a laser lamp.

\* \* \* \* \*